(12) United States Patent
Frederickson et al.

(10) Patent No.: US 10,307,578 B2
(45) Date of Patent: Jun. 4, 2019

(54) MICRONEEDLE CARTRIDGE ASSEMBLY AND METHOD OF APPLYING

(71) Applicant: 3M INNOVATIVE PROPERTIES COMPANY, St. Paul, MN (US)

(72) Inventors: Franklyn L. Frederickson, White Bear Lake, MN (US); Michael D. Johnson, College Station, TX (US)

(73) Assignee: 3M Innovative Properties Company, St. Paul, MN (US)

( * ) Notice: Subject to any disclaimer, the term of this patent is extended or adjusted under 35 U.S.C. 154(b) by 54 days.

(21) Appl. No.: 15/606,753

(22) Filed: May 26, 2017

(65) Prior Publication Data

US 2017/0266428 A1    Sep. 21, 2017

Related U.S. Application Data

(62) Division of application No. 11/917,442, filed as application No. PCT/US2006/024672 on Jun. 23, 2006, now abandoned.

(60) Provisional application No. 60/694,446, filed on Jun. 27, 2005.

(51) Int. Cl.
*A61M 37/00* (2006.01)

(52) U.S. Cl.
CPC . *A61M 37/0015* (2013.01); *A61M 2037/0023* (2013.01)

(58) Field of Classification Search
CPC ................ A61M 25/002; A61M 5/002; A61M 37/0015; A61M 2037/0023; A61M 2037/0046; A61M 2037/0061
See application file for complete search history.

(56) References Cited

U.S. PATENT DOCUMENTS

| 3,072,122 A | 1/1963 | Rosenthal |
| 3,630,346 A | 12/1971 | Burnside |
| 3,678,150 A | 7/1972 | Szumski et al. |
| 3,964,482 A | 6/1976 | Gerstel et al. |
| 4,381,963 A | 5/1983 | Goldstein et al. |

(Continued)

FOREIGN PATENT DOCUMENTS

| JP | 62-148421 | 7/1987 | ............... A61K 9/70 |
| JP | 2-84622 | 7/1990 | ............. A61F 13/02 |

(Continued)

OTHER PUBLICATIONS

Daddona, Current Opinion in Drug Discovery and Development 1999 2(2);168-171.

(Continued)

*Primary Examiner* — Laura A Bouchelle
(74) *Attorney, Agent, or Firm* — Eric E. Silverman (57) ABSTRACT

A microneedle array cartridge includes a web of material having a top face and an opposite bottom face. An adhesive and a microneedle array are disposed on the bottom face of the web of material. A container is disposed relative to the bottom face of the web of material, and has a perimeter portion and a central portion for covering at least part of the microneedle array. At least part of the perimeter portion of the container contacts the adhesive, and the central portion of the container does not contact the adhesive. The perimeter portion and the central portion of the container are integrally formed.

12 Claims, 8 Drawing Sheets

(56) References Cited

U.S. PATENT DOCUMENTS

| | | | |
|---|---|---|---|
| 4,382,513 A | 5/1983 | Schirmer | B29C 65/76 206/484 |
| 4,656,068 A | 4/1987 | Raines | |
| 4,666,441 A | 5/1987 | Andriola et al. | 604/897 |
| 5,152,917 A | 10/1992 | Pieper et al. | |
| 5,160,823 A | 11/1992 | Bennin et al. | |
| 5,223,261 A | 6/1993 | Nelson et al. | |
| 5,250,023 A | 10/1993 | Lee et al. | 604/20 |
| 5,256,360 A | 10/1993 | Li | |
| 5,342,737 A | 8/1994 | Georger, Jr. et al. | |
| 5,376,317 A | 12/1994 | Maus et al. | |
| 5,380,760 A | 1/1995 | Wendel et al. | |
| 5,543,108 A | 8/1996 | Bacher et al. | |
| 5,591,139 A | 1/1997 | Lin et al. | |
| 5,611,806 A | 3/1997 | Jang | |
| 5,620,095 A * | 4/1997 | Delmore | A61F 15/001 206/438 |
| 5,645,977 A | 7/1997 | Wu et al. | |
| 5,656,286 A | 8/1997 | Miranda et al. | |
| 5,657,516 A | 8/1997 | Berg et al. | |
| 5,658,515 A | 8/1997 | Lee et al. | |
| 5,783,269 A | 7/1998 | Heilmann et al. | |
| 5,879,326 A | 3/1999 | Godshall et al. | |
| 5,983,136 A | 11/1999 | Kamen | |
| 6,050,988 A | 4/2000 | Zuck | |
| 6,076,248 A | 6/2000 | Hoopman et al. | |
| 6,091,975 A | 7/2000 | Daddona et al. | |
| 6,129,540 A | 10/2000 | Hoopman et al. | |
| 6,132,755 A | 10/2000 | Eicher et al. | |
| 6,256,533 B1 | 7/2001 | Yuzhakov et al. | |
| 6,312,612 B1 | 11/2001 | Sherman et al. | |
| 6,322,808 B1 | 11/2001 | Trautman et al. | |
| 6,331,266 B1 | 12/2001 | Powell et al. | |
| 6,334,856 B1 | 1/2002 | Allen et al. | |
| 6,379,324 B1 | 4/2002 | Gartstein et al. | |
| 6,451,240 B1 | 9/2002 | Sherman et al. | |
| 6,454,755 B1 | 9/2002 | Godshall | |
| 6,499,595 B1 * | 12/2002 | Petricca | A45D 27/225 206/356 |
| 6,503,231 B1 | 1/2003 | Prausnitz et al. | |
| 6,511,463 B1 | 1/2003 | Wood et al. | |
| 6,532,386 B2 | 3/2003 | Sun et al. | |
| 6,533,949 B1 | 3/2003 | Yeshurun et al. | |
| 6,551,849 B1 | 4/2003 | Kenney | |
| 6,565,532 B1 | 5/2003 | Yuzhakov et al. | |
| 6,591,124 B2 | 7/2003 | Sherman et al. | |
| 6,595,947 B1 | 7/2003 | Mikszta et al. | |
| 6,603,998 B1 | 8/2003 | King et al. | |
| 6,605,332 B2 | 8/2003 | Calhoun et al. | |
| 6,652,478 B1 | 11/2003 | Gartstein et al. | |
| 6,663,820 B2 | 12/2003 | Arias et al. | |
| 6,686,299 B2 | 2/2004 | Montemagno et al. | |
| 6,713,291 B2 | 3/2004 | King et al. | |
| 6,743,211 B1 | 6/2004 | Prausnitz et al. | |
| 6,770,480 B1 | 8/2004 | Canham | |
| 6,797,276 B1 | 9/2004 | Glenn et al. | |
| 6,835,184 B1 | 12/2004 | Sage et al. | |
| 6,881,203 B2 | 4/2005 | Delmore et al. | |
| 6,899,838 B2 | 5/2005 | Lastovich | |
| 6,908,453 B2 | 6/2005 | Fleming et al. | |
| 6,931,277 B1 | 8/2005 | Yuzhakov et al. | |
| 2002/0045859 A1 | 4/2002 | Gartstein et al. | |
| 2002/0053756 A1 | 5/2002 | Powell et al. | |
| 2002/0082543 A1 | 6/2002 | Park et al. | |
| 2002/0091357 A1 | 7/2002 | Trautman et al. | |
| 2002/0095134 A1 | 7/2002 | Pettis et al. | |
| 2002/0138049 A1 | 9/2002 | Allen et al. | |
| 2002/0169416 A1 | 11/2002 | Gonnelli et al. | |
| 2002/0177858 A1 | 11/2002 | Sherman et al. | |
| 2002/0198509 A1 | 12/2002 | Mikszta et al. | |
| 2003/0045837 A1 | 3/2003 | Delmore et al. | |
| 2003/0078549 A1 | 4/2003 | Stupar et al. | |
| 2003/0095582 A1 | 5/2003 | Ackley | |
| 2003/0135161 A1 * | 7/2003 | Fleming | A61B 5/14514 604/173 |
| 2003/0135166 A1 | 7/2003 | Gonnelli | |
| 2003/0135167 A1 | 7/2003 | Gonnelli | |
| 2003/0135201 A1 | 7/2003 | Gonnelli | |
| 2003/0148401 A1 | 8/2003 | Agrawal et al. | |
| 2003/0199810 A1 | 10/2003 | Trautman et al. | |
| 2004/0049150 A1 | 3/2004 | Dalton et al. | |
| 2004/0060902 A1 | 4/2004 | Evans et al. | |
| 2004/0176732 A1 | 9/2004 | Frazier et al. | |
| 2005/0025778 A1 | 2/2005 | Cormier et al. | |
| 2005/0065463 A1 | 3/2005 | Tobinaga et al. | |
| 2005/0106226 A1 | 5/2005 | Cormier et al. | |
| 2005/0118388 A1 | 6/2005 | Kingsford | |
| 2005/0137525 A1 | 6/2005 | Wang et al. | |
| 2005/0228340 A1 | 10/2005 | Cleary et al. | 604/46 |
| 2005/0261631 A1 | 11/2005 | Clarke et al. | |
| 2007/0250018 A1 | 10/2007 | Adachi et al. | 604/239 |

FOREIGN PATENT DOCUMENTS

| | | | |
|---|---|---|---|
| JP | 3-151982 | 6/1991 | A61M 5/28 |
| JP | 8-503910 | 4/1996 | |
| JP | 2004-114552 | 4/2004 | |
| JP | 2005-514179 | 5/2005 | A61M 37/00 |
| WO | WO 1994/07761 | 4/1994 | |
| WO | WO 96/10630 | 4/1996 | |
| WO | WO 1998/28037 | 7/1998 | |
| WO | WO 00/45798 | 8/2000 | |
| WO | WO 01/36037 | 5/2001 | |
| WO | WO 02/28471 | 4/2002 | |
| WO | WO 2002/28471 | 4/2002 | |
| WO | WO2003-059431 | 7/2003 | A61M 37/00 |
| WO | WO 2003/074102 | 9/2003 | |
| WO | WO 04/009470 | 1/2004 | |
| WO | WO 2004/009172 | 1/2004 | |
| WO | WO 05/51455 | 6/2005 | |
| WO | WO2006-016647 | 2/2006 | A61M 37/00 |
| WO | WO 07/002521 | 1/2007 | |

OTHER PUBLICATIONS

Edwards. Proceedings of SPIE vol. 4177.
Griss et al. IEEE 2002, pp. 467-470.
Henry et al. J. Pharm.Sci., 1998, 87,8,922-925.
Kaushik et al. Anesthesia Analg., 2001, 92, 502-504.
Mcallister et al. Annual Review of Biomedical Engineering, 2000, 2, 289-313.
Mcallister et al. Proceed. Int'l. Symp. Control Release of Bioactive Material, 26, (1999), CRS, 192-193.
Weber et al. Proceedings of SPIE vol. 2879, p. 156.

* cited by examiner

MICRONEEDLE CARTRIDGE ASSEMBLY AND METHOD OF APPLYING

CROSS-REFERENCE TO RELATED APPLICATIONS

The present application is a divisional application of U.S. patent application Ser. No. 11/917,412, filed Dec. 13, 2007, which is a National Stage Entry of PCT/US2006/024672, filed Jun. 23, 2006, which claims priority to U.S. Provisional Application Ser. No. 60/694,446, filed on Jun. 27, 2005, each of which is incorporated herein in its entirety.

FIELD

The present invention relates to microneedle array cartridges.

BACKGROUND

Only a limited number of molecules with demonstrated therapeutic value can be transported through the skin via unassisted or passive transdermal drug delivery. The main barrier to transport of molecules through the skin is the stratum corneum (the outermost layer of the skin).

Devices including arrays of relatively small structures, sometimes referred to as microneedles or micro-pins, have been disclosed for use in connection with the delivery of therapeutic agents and other substances through the skin and other surfaces. The devices are typically pressed against the skin in an effort to pierce the stratum corneum. The microneedle arrays are generally used once and then discarded.

Microneedles on these devices pierce the stratum corneum upon contact, making a plurality of microscopic slits that serve as passageways through which molecules of active components (e.g., therapeutic agents, vaccines, and other substances) can be delivered into the body. In delivering an active component, the microneedle array can be provided with a reservoir for temporarily retaining an active component in liquid form prior to delivering the active component through the stratum corneum. In some constructions, the microneedles can be hollow to provide a liquid flow path directly from the reservoir and through the microneedles to enable delivery of the therapeutic substance through the skin. In alternate constructions, active component(s) may be coated and dried on the microneedle array and delivered directly through the skin after the stratum corneum has been punctured.

Transdermal adhesive patches are also available and are generally constructed as an adhesive article with a pressure sensitive adhesive coated onto the surface of a backing comprised of a polymeric film, cloth or the like. Transdermal adhesive patches are provided with an adhesive that allows the patch to be releasably adhered to the surface of the skin where a predetermined dosage of an active component can be put in contact with a small surface area of the skin. An appropriate biocompatible carrier is normally provided to facilitate the absorption of molecules through the stratum corneum over a period of time while the patch remains adhered to the skin.

BRIEF SUMMARY

Patches, with or without a microneedle array, can have fragile and sanitary characteristics. It is generally desired that the patch and array not be contacted before application to a target site. This presents difficulties in storing and transporting patches to desired locations for eventual application. In addition, providing collars or other protection for microneedle arrays produces bulky structures that require excessive amounts of materials to manufacture and take up large amounts of space during transportation and storage. Moreover, loading a microneedle array on an applicator device can also be time consuming and difficult for operators. Thus, the present invention provides an alternative microneedle cartridge design.

In a first aspect of the present invention, a microneedle array cartridge includes a web of material having a top face and an opposite bottom face. An adhesive and a microneedle array are disposed on the bottom face of the web of material. A container is disposed relative to the bottom face of the web of material, and has a perimeter portion and a central portion for covering at least part of the microneedle array. At least part of the perimeter portion of the container contacts the adhesive, and the central portion of the container does not contact the adhesive. The perimeter portion and the central portion of the container are integrally formed.

In another aspect of the present invention, a microneedle array package includes a plurality of adhesive patches separably attached to each other, and each of the adhesive patches carrying a microneedle array.

In another aspect of the present invention, a microneedle array cartridge includes a web of material having a top face and an opposite bottom face, an adhesive, a microneedle array and a container. The web of material is disposed substantially in a first plane. The adhesive is disposed on the bottom face of the web of material. The microneedle array is disposed relative to the bottom face of the web of material. The container is disposed relative to the bottom face of the web of material, and has a perimeter portion and a central portion for covering at least a portion of the microneedle array. A first region of the perimeter portion is disposed substantially in a second plane that is generally parallel to the first plane, and a second region of the perimeter portion is generally not disposed in the second plane.

In another aspect of the present invention, a microneedle array cartridge includes a web of material having a top face, an opposite bottom face and defining a perimeter, an adhesive disposed on the bottom face of the web of material, a microneedle array, and a container. The microneedle array is disposed relative to the bottom face of the web of material. The container is disposed relative to the bottom face of the web of material, and has a perimeter portion and a central portion for covering at least a portion of the microneedle array. The perimeter portion of the container generally extends at least to the perimeter of the web of material, and has a pair of opposing cutout regions that do not extend as far as the perimeter of the web of material.

In another aspect of the present invention, a microneedle array cartridge includes a web of material having a top face, an opposite bottom face and defining a perimeter, an adhesive disposed on the bottom face of the web of material, a microneedle array, and a container. The microneedle array is disposed relative to the bottom face of the web of material. The container extends only from the bottom face of the web of material, and has a perimeter portion and a central portion for covering at least part of the microneedle array. At least part of the perimeter portion of the container contacts the adhesive and the central portion does not contact the adhesive.

In another aspect of the present invention, a method for microneedle array application includes slidably mounting a microneedle array cartridge on an applicator device, simultaneously exposing the microneedle array of the cartridge by removing a cover portion of the cartridge when the cartridge is at least partially mounted on the applicator device, and moving the microneedle array toward a target site.

In another aspect of the present invention, a method of mounting a microneedle array relative to a microneedle array application device includes slidably positioning a microneedle cartridge having a microneedle array and a removable cover at least partially within a retaining portion of the microneedle array application device, rotating the microneedle cartridge relative to the microneedle array application device within the retaining portion of the microneedle array application device in order to break a seal to allow removal of the cover, and exposing the microneedle array of the microneedle cartridge by removing the cover when the microneedle cartridge is at least partially mounted on the microneedle array applicator device.

The above summary is not intended to describe each disclosed embodiment or every implementation of the present invention. The figures and the detailed description, which follow, more particularly exemplify illustrative embodiments.

While the above-identified drawing figures set forth several embodiments of the invention, other embodiments are also contemplated, as noted in the discussion. In all cases, this disclosure presents the invention by way of representation and not limitation. It should be understood that numerous other modifications and embodiments can be devised by those skilled in the art, which fall within the scope and spirit of the principles of the invention. The figures may not be drawn to scale. Like reference numbers have been used throughout the figures to denote like parts.

DETAILED DESCRIPTION

Patches can be used for transdermal delivery of molecules, and can carry microneedle arrays, which have utility for the delivery of large molecules that are ordinarily difficult to deliver by passive transdermal delivery. As used herein, "array" refers to the medical devices described herein that include one or more structures capable of piercing the stratum corneum to facilitate the transdermal delivery of therapeutic agents or the sampling of fluids through or to the skin. "Microstructure," "microneedle" or "microarray" refers to the specific microscopic structures associated with the array that are capable of piercing the stratum corneum to facilitate the transdermal delivery of therapeutic agents or the sampling of fluids through the skin. By way of example, microstructures can include needle or needle-like structures as well as other structures capable of piercing the stratum corneum. The microneedles are typically less than 500 microns in height, and sometimes less than 300 microns in height. The microneedles are typically more than 20 microns in height, often more than 50 microns in height, and sometimes more than 125 microns in height.

Figure 1:
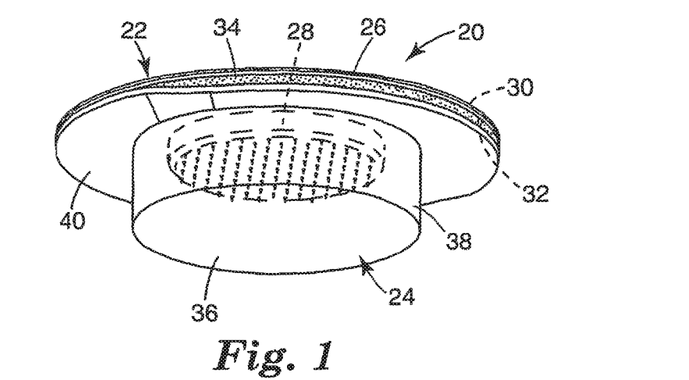
FIG. 1 is a perspective view of a first embodiment of a microneedle cartridge.
Figure 2:
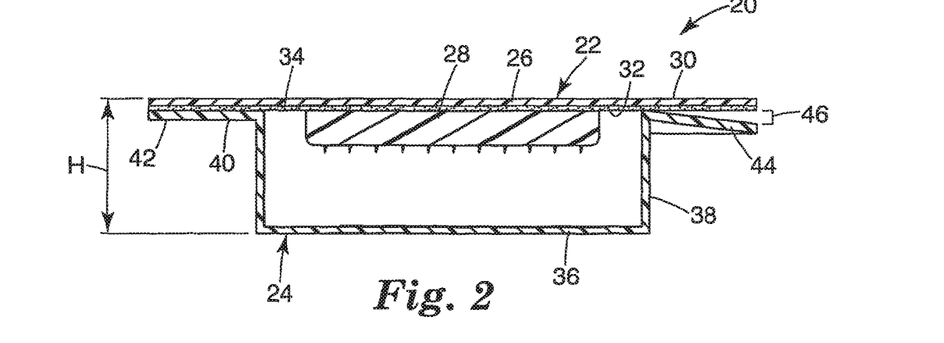
FIG. 2 is a cross-sectional view of the microneedle cartridge of FIG. 1.

FIG. 1 is a perspective view of a first embodiment of a microneedle cartridge 20 that includes a patch 22 and a container 24. FIG. 2 is a cross-sectional view of the microneedle cartridge 20. The patch 22 shown in FIGS. 1 and 2 includes a web of material 26 that forms a backing, and a microneedle array 28 supported by and attached to the web of material 26. The web of material 26 is generally flat, and has an upper face 30 and a lower face 32. The web of material 26 can be comprised of a polymeric film, cloth, nonwoven or the like. An adhesive 34, such as a pressure sensitive adhesive, is disposed on the lower face 32 of the web of material 26. The microneedle array 28 is located relative to the lower face 32 of the web of material 26 at a generally central portion of the web of material 26, which has a circular shape. The microneedle array 28 can be attached to the web of material 26, for example, by adhesive, welding, heat bonding, and can be formed integrally with the web of material 26.

Suitable materials for the microneedle array 28 include those selected from materials such as acrylonitrile-butadiene-styrene (ABS) polymers, polyphenyl sulfides, polycarbonates, polypropylenes, acetals, acrylics, polyetherimides, polybutylene terephthalates, polyethylene terephthalates as well as other known materials and combinations of two or more of the foregoing. The microneedle array 28 can carry molecules for eventual delivery through the stratum corneum of a patient's skin (i.e., the skin of a human or non-human test subject). Those molecules can be therapeutic agents, vaccines, and other materials. A reservoir can be included with the microneedle array 28 for holding molecules for eventual delivery. Deployment of the patch 22 to a target site permits the molecules to be delivered through or to the stratum corneum.

The adhesive layer will generally be selected according to the desired end use of the articles prepared by the present method. Examples of suitable adhesives include acrylates, silicones, polyisobutylenes, synthetic rubber, natural rubber, and copolymers and mixtures thereof. Further description of suitable adhesives may be found in U.S. Pat. No. 5,656,286 (Miranda et al.), U.S. Pat. No. 4,693,776 (Krampe et al.), U.S. Pat. No. 5,223,261. (Nelson et al.), and U.S. Pat. No.

5,380,760 (Wendel et al.) the disclosures of which are incorporated herein by reference.

Typical examples of flexible films employed as conventional tape backings which may be useful as a backing film include those made from polymer films such as polypropylene; polyethylene, particularly low density polyethylene, linear low density polyethylene, metallocene polyethylenes, and high density polyethylene; polyvinyl chloride; polyester (e.g., polyethylene terephthalate); polyvinylidene chloride; ethylene-vinyl acetate (EVA) copolymer; polyurethane; cellulose acetate; and ethyl cellulose. Coextruded multilayer polymeric films are also suitable, such as described in U.S. Pat. No. 5,783,269 (Heilmann et al.), the disclosure of which is incorporated herein by reference. Layered backings such as polyethylene terephthalate-aluminum-polyethylene composites and polyethylene terephthalate-EVA composites are also suitable. Foam tape backings, such as closed cell polyolefin films used in 3M™ 1777 Foam Tape and 3M™ 1779 Foam Tape are also suitable. Polyethylenes, polyethylene blends, and polypropylenes are preferred polymer films. Polyethylenes and polyethylene blends are most preferred polymer films. In one embodiment, the backing film is translucent or transparent. Additives may also be added to the backing film, such as tackifiers, plasticizers, colorants, and anti-oxidants.

The container 24 is removably attached to the patch 22 to cover the microneedle array 28. The container 24 includes a circular central base portion 36, a sidewall 38 connected at or near the perimeter of the central base portion 36, and a perimeter lip 40 connected to the sidewall 38 opposite the central base portion 36. A first portion 42 of the perimeter lip 40 is adhesively affixed to the adhesive 34 on the web of material 26, and a second portion 44 of the perimeter lip 40 is spaced from the adhesive 34 so as not to adhere to it. This creates a gap or slight separation 46 (see FIG. 2). The gap 46 facilitates separating the container 24 from the patch 22 for application of the patch 22 to a patient. However, in one embodiment, a continuous adhesive connection is formed around the microneedle array 28 between the web of material 26 and the perimeter lip 40 of the container 24. That continuous connection can form a seal. In some instances, the seal may be a hermetic seal, that is, a seal that can prevent entry or escape of air or other vapors, such as moisture vapor. Sealing the microneedle array 28 between the web of material 26 and the container 24 helps protect the microneedle array 28 from contamination and damage prior to deployment. In such a configuration the web of material 26 may be considered to be disposed substantially in a first plane and the first portion 42 of the perimeter lip 40 is disposed substantially in a second plane that is generally parallel to the first plane. It should be understood by the term disposed substantially in a plane, that the web 26 and first portion 42 are largely planar, but that minor variations, for example, due to manufacturing imperfections or due to the flexibility in the web and/or the carrier material may cause slight, but insignificant, deviations from planarity. The second portion 44 of the perimeter lip 40 is generally not disposed in the second plane.

As shown, the shape of the container is a cylinder, but it should be understood that other shapes are suitable as long as the base portion is appropriately spaced from the microneedle array 28. For example, the central base portion 36 and sidewall 38 may have the form of a dome, in which case there may be no discernable boundary between the sidewall 38 and the central base portion 36. The sidewalls may be angled and in some embodiments may extend until they contact an opposing sidewall, for example, forming a cone-shaped container. Furthermore, the container may have additional exterior protrusions or indentations to facilitate handling and/or storage. For example, a handling tab may be affixed to the exterior surface of the base portion to make the container more easily graspable.

The central base portion 36 and the sidewall 38 of the container 24 define a volume in which the microneedle array 28 can rest. The container 24 is spaced from the microneedle array 28, as the microneedle array 28 is generally susceptible to damage from contact during storage, transportation, and at other times prior to deployment. The container 24 can have a relatively low profile, such that the sidewall 38 of the container 24 preferably has as small a height, H, as possible without damaging or risking damage to the microneedle array 28 through contact. A low profile container 24 reduces space occupied by the cartridge 20, for storage and transportation purposes, while still providing protection to the microneedle array 28. A low profile container 24 also reduces the amounts of gases (i.e., air) and contaminants that are exposed to the microneedle array 28 and molecules carried thereon. Because many molecules intended for delivery with the microneedle array 28 can have limited lifespans and may be sensitive to contamination and deterioration, a low profile container 24 reduces the volume of air that is exposed to the microneedle array 28 to limit such negative effects. A suitable low-profile height will depend upon the nature of the patch 22 and microneedle array 28, but the height will typically be less than 2.0 cm, often less than 1.5 cm, and sometimes less than 1.0 cm.

The container 24 can be formed of a polymer material. Generally, a rigid material is selected in order to better protect the microneedle array 28 from damage and to facilitate storage (e.g., for stacking a plurality of microneedle cartridges 20). In one embodiment, the container 24 is a transparent or translucent material. In one embodiment, the container 24 is opaque to protect the microneedle array 28 from exposure to light.

Figure 3:
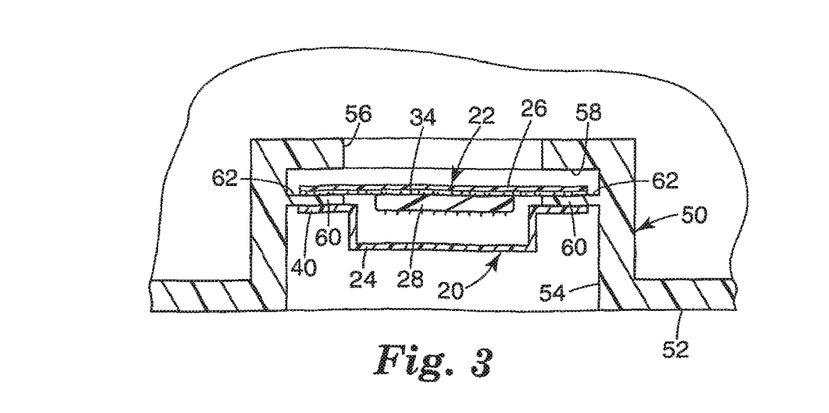
FIG. 3 is a partial cross-sectional view of the microneedle cartridge of FIGS. 1 and 2 mounted on an applicator device.

FIG. 3 is a partial cross-sectional view of the microneedle cartridge 20 held on an applicator device 50. As shown in FIG. 3, the applicator device 50 has a skin-contacting face 52, a recess 54, a substantially circular opening 56 defined in a bottom portion 58 of the recess 54, and a pair of retainer members 60 that each have substantially flat upper surfaces 62. The retainer members 60 are generally elongate and their substantially flat upper surfaces 62 are generally parallel to and facing the bottom portion 58 of the recess 54. The pair of retainer members 60 are located at opposite portions of the opening 56 and are connected at one side of the recess 54. The retainer members 60 define an opening at one end for accepting patches between the retainer members 60 and the bottom portion 58 of the recess 54. The upper surfaces 62 of the retainer members 60 may be non-stick or release surfaces. A non-stick or release surface can be achieved, for example, by a non-stick or release coating applied to the upper surfaces 62. The non-stick or release coating can be selected according to the desired use of the applicator device 50. For instance, a release coating, such as a low surface energy silicone, fluoropolymer, or fluoro-silicone release coating, can be selected based upon the adhesives used with patches applied using the patch application device 50

As shown in FIG. 3, the patch 22 is disposed between the retainer members 60 and the bottom portion 58 of the recess 54. The microneedle array 28 carried by the patch 22 faces away from opening 56 in the applicator device 50. The patch 22 contacts the upper surfaces 62 of the retainer members 60, but generally does not adhere firmly to the retainer members 60 due to the non-stick or release character of the upper surfaces 62.

Figure 4:
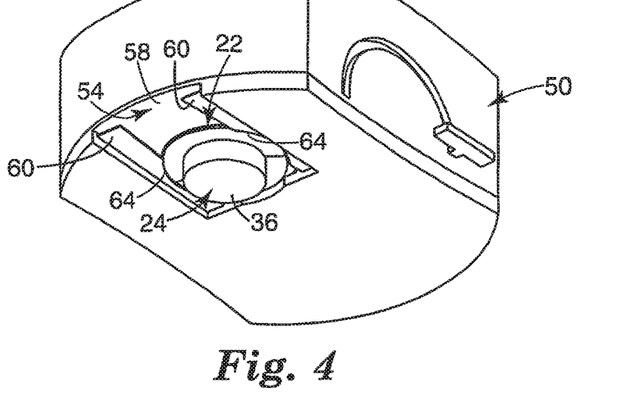
FIG. 4 is a perspective view of the patch of FIGS. 1, 2 and 3 mounted on the applicator device of FIG. 3.

FIG. 4 is a perspective view of the patch 22 mounted on the applicator device 50. In a fully mounted position, as shown in FIG. 4, the patch 22 is generally aligned relative to the opening 56 in the applicator device 50 (the opening 56 is not visible in FIG. 4). The retainer members 60 have cutaway portions 64 that provide an enlarged, partially circular open region that is generally aligned with the opening 56 on the bottom portion 58 of the recess 54. The open region defined by the cutaway portions 64 facilitates patch application by reducing the amount of deflection of the patch 22 required to move the patch 22 from a mounted position on the applicator device 50 to a target location, during deployment. Further details of applicators suitable for use with microneedle array cartridges of the present invention may be found in U.S. Patent Application Ser. No. 60/694,447 filed on Jun. 27, 2005, the disclosure of which is hereby incorporated by reference.

Figure 13:
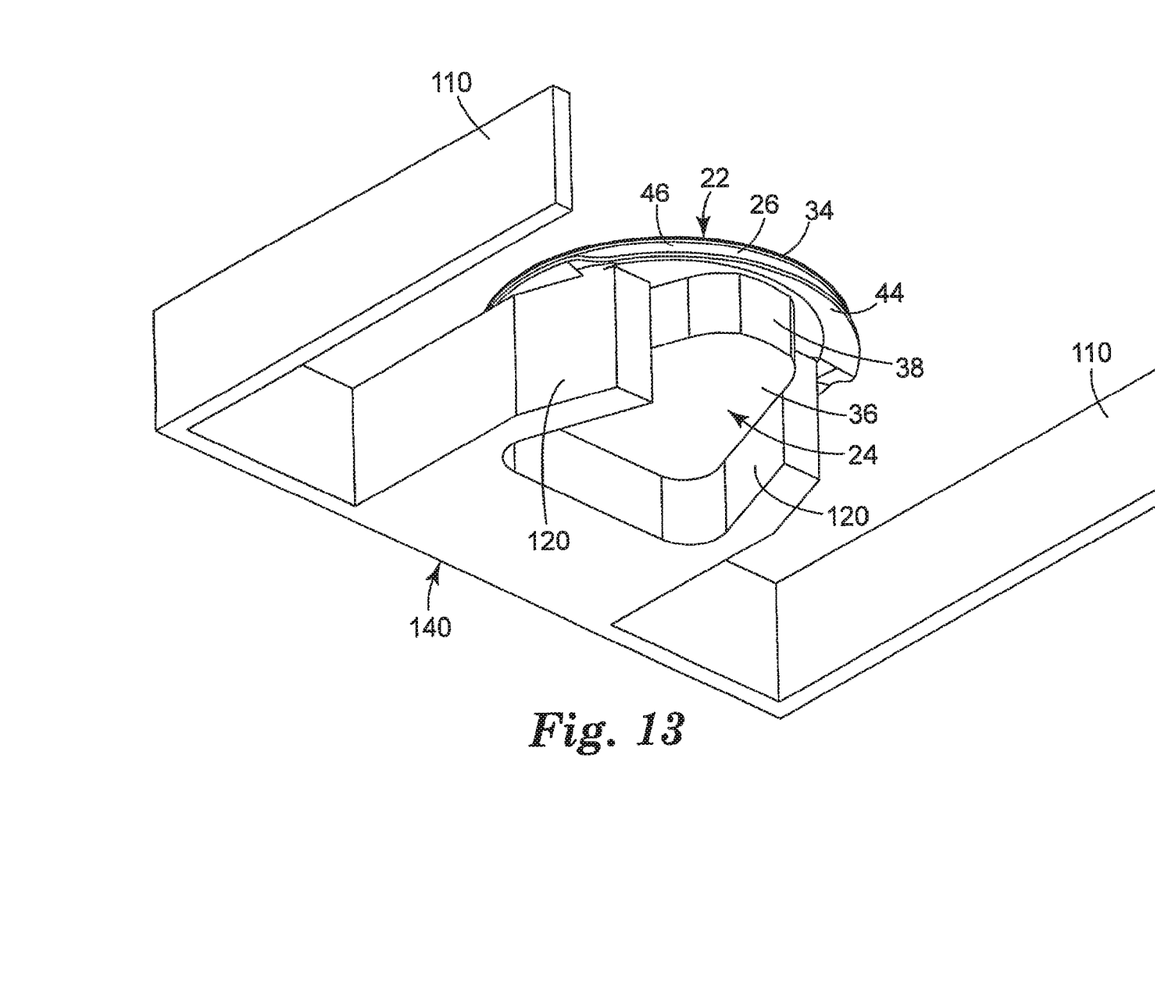
FIG. 13 is a bottom perspective view of a microneedle cartridge in a mounting fixture.
Figure 14:
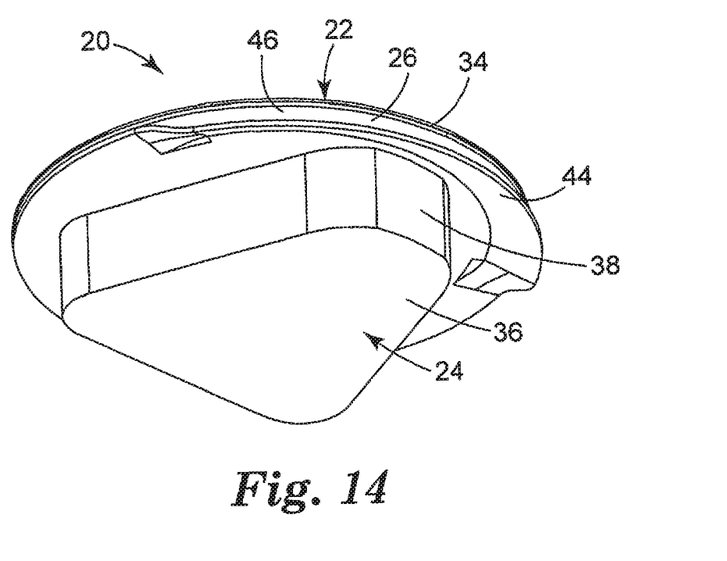
FIG. 14 is a bottom perspective view of another embodiment of a microneedle cartridge.

The microneedle cartridge 20 allows for simple and easy mounting of the patch 22 to the applicator device 50, for eventually applying the microneedle array 28 (the array 28 is not visible in FIG. 4) to a target site. Mounting the microneedle patch 22 on the applicator device 50 includes the following steps. First, the microneedle cartridge 20, with the container 24 affixed thereto, is partially slid onto the retainer members 60. Ends of the retainer members 60 are positioned in the gap 46 formed between the web of material 26 and the perimeter lip 40 of the container 24 of the microneedle cartridge 20. Then the microneedle cartridge 20 is slid further along the retainer members 60, simultaneously separating the container 24 from the web of material 26, until the patch 22 is fully mounted on the applicator device 50 (e.g., such that the microneedle array 28 is aligned with the opening 56 defined in the bottom portion 58 of the recess 54). The container 24 is removed from (i.e., separated from) the patch 22 to uncover and expose the microneedle array 28 prior to microneedle deployment. An operator may need to pull the container 24 away from the applicator device 50 (e.g., by applying a force perpendicular to the skin-contacting face 52 of the applicator device 50) in order to fully separate the container 24 from the patch 22, during the process of mounting or once mounted onto an applicator device. The motion between the microneedle cartridge 20 and the applicator device 50 is a relative motion which may be accomplished by moving one or both of the applicator device 50 and the microneedle cartridge 20. In one embodiment, a mounting fixture 100 may be used to assist in mounting the patch 22 of the microneedle cartridge 20 to the applicator device 50. A perspective view of the bottom of a mounting fixture 100 is shown in FIG. 13. The mounting fixture 100 comprises alignment members 110 and cartridge holder members 120. The cartridge 20 (shown in more detail in FIG. 14) includes a patch 22 and a container 24. The patch 22 includes a web of material 26 that forms a backing, and a microneedle array 28 (not shown) supported by and attached to the web of material 26. An adhesive 34, such as a pressure sensitive adhesive, is disposed on the lower face 32 of the web of material 26. The container 24 is removably attached to the patch 22 to cover the microneedle array 28. The container 24 includes an asymmetric central base portion 36, a sidewall 38 connected at or near the perimeter of the central base portion 36, and a perimeter lip 40 connected to the sidewall 38 opposite the central base portion 36. A second portion 44 of the perimeter lip 40 is spaced from the adhesive 34 so as not to adhere to it. This creates a gap or slight separation 46. The gap 46 facilitates separating the container 24 from the patch 22 for application of the patch 22 to a patient. The asymmetric shape of the central base portion 36 may be selected so as to mate with the opening provided by the cartridge holder members 120 in an orientation that presents the gap 46 to the front of the mounting fixture 100. This prevents the user from accidentally misaligning the gap 46 with respect to the applicator device 50.

Figure 15:
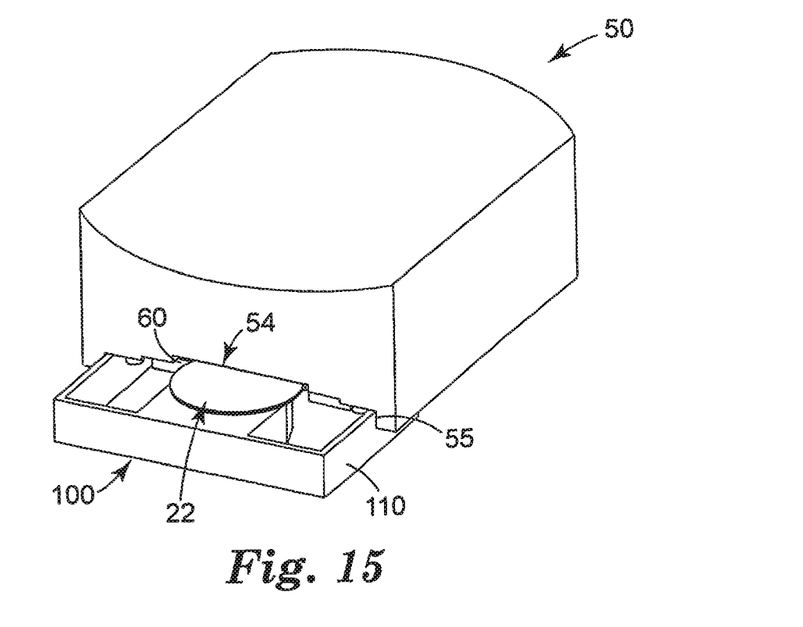
FIG. 15 is a top perspective view of a mounting fixture and microneedle cartridge partially inserted into an applicator.
Figure 16:
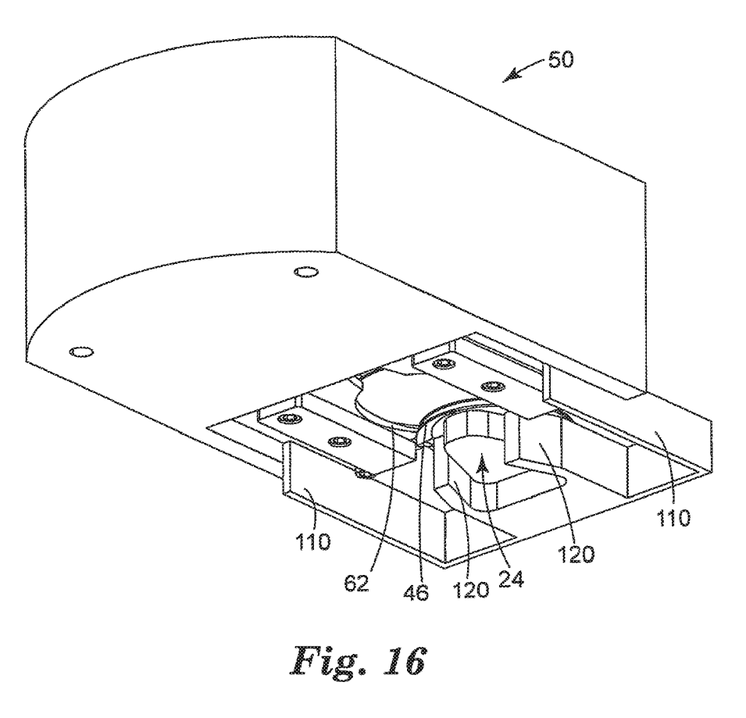
FIG. 16 is bottom perspective view of a mounting fixture and microneedle cartridge partially inserted into an applicator.

The mounting fixture 100 with mounted cartridge 20 is shown partially mated with an applicator device 50 in FIGS. 15 and 16. The alignment guides 110 contact an outer recess 55, thus providing for alignment of the cartridge 20 with the retainer members 60 of the applicator 50. The mounting fixture may be used to fully insert the cartridge 20 into the applicator 50, at which time the mounting fixture 100 and container 24 may be removed, thereby leaving the patch 22 mounted in the applicator 50. In one embodiment, the mounting fixture may be easily grasped by a user or otherwise fixed in space, so that the user may bring the applicator 50 towards the stationary mounting fixture to load the patch 22 into the applicator 50. For example, the mounting fixture 100 may be part of a base station that holds multiple cartridges 20 and advances them to the cartridge holder members 120 one at a time. In another embodiment, the mounting fixture 100 may be integrated with packaging material used to hold one or more cartridges 20. For example, a box of cartridges may have a mounting fixture affixed to an outside surface so that a user could remove a cartridge from the box, place the cartridge in the mounting fixture, and load the cartridge into the applicator as described above. In still another embodiment, a tray holding multiple cartridges could be provided, wherein each cartridge is held in a mounting fixture integrally molded into the tray. Thus each cartridge could be directly loaded from the tray into an applicator.

The mounting configuration shown in FIGS. 3 and 4 is provided by way of example, and not limitation. In further embodiments, other means of mounting a patch on the applicator device can be used. For instance, in further embodiments, one or more patches can be stored inside the applicator device 50 prior to application, and then dispensed for application to a target site.

Figure 5:
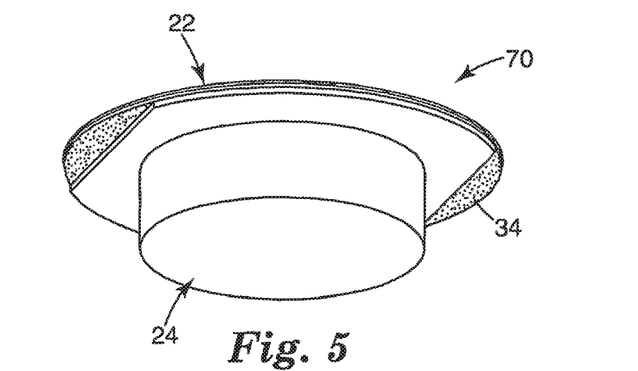
FIG. 5 is a perspective view of a second embodiment of a microneedle cartridge.
Figure 6:
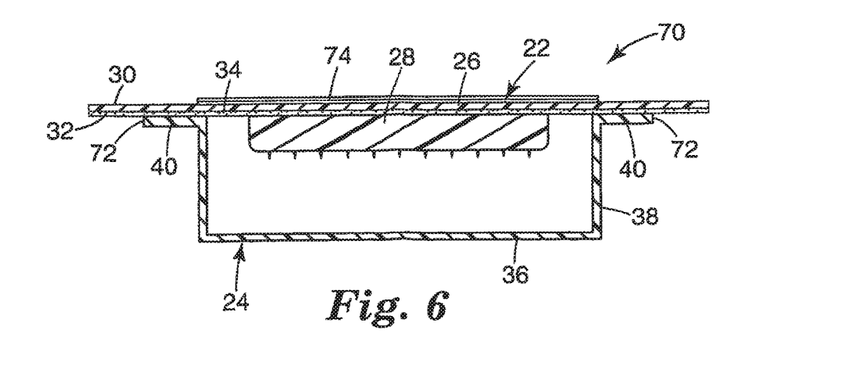
FIG. 6 is a front cross-sectional view of the microneedle cartridge of FIG. 5.
Figure 7:
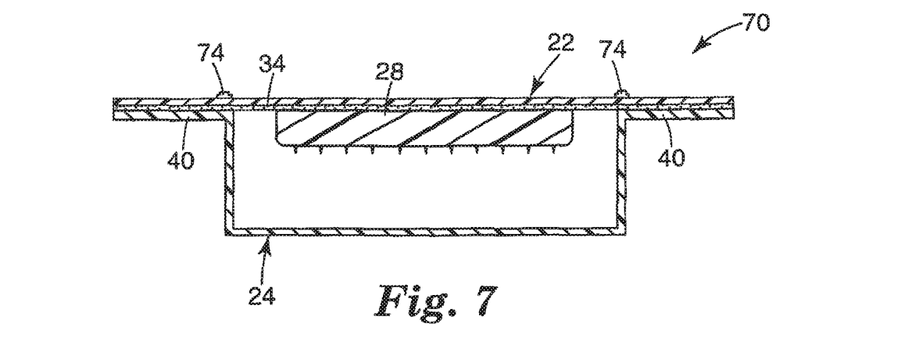
FIG. 7 is a side cross-sectional view of the microneedle cartridge of FIGS. 6 and 7, rotated 90° relative to FIG. 6.
Figure 8:
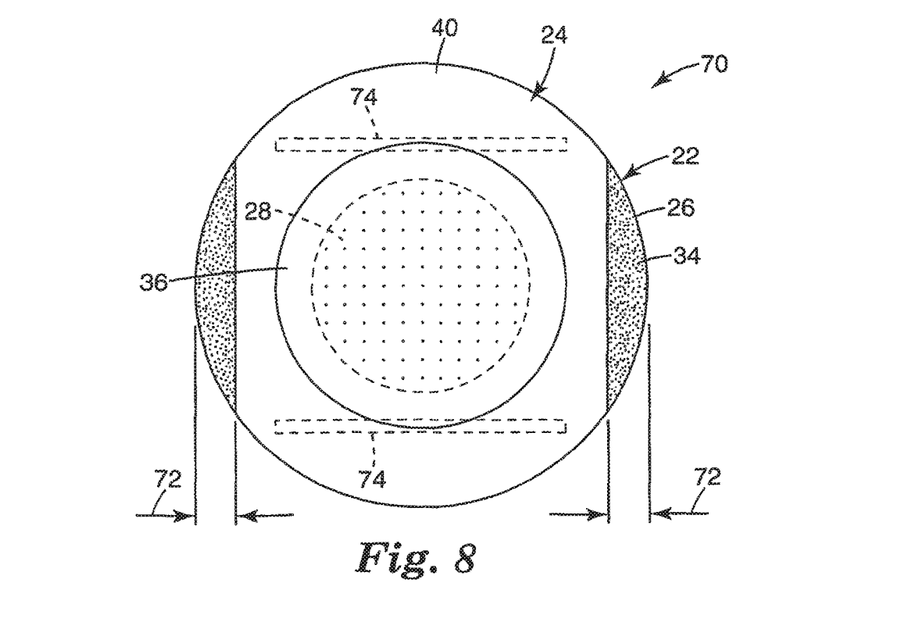
FIG. 8 is a bottom view of the microneedle cartridge of FIGS. 5, 6 and 7.

FIGS. 5-8 show a second embodiment of a microneedle cartridge 70. FIG. 5 is a perspective view of the microneedle cartridge 70. FIG. 6 is a front cross-sectional view of the microneedle cartridge 70, and FIG. 7 is a side cross-sectional view of the microneedle cartridge 70. FIG. 8 is a bottom view of the microneedle cartridge 70.

The microneedle cartridge 70 includes a patch 22 and a container 24. The patch 22 includes a web of material 26, a microneedle array 28 and an adhesive 34 on a bottom face 32 of the web of material 26, and is generally similar to that shown and described with respect to FIGS. 1-4 above. The container 24 is removably attached to the patch 22 to cover the microneedle array 28. The container 24 includes a circular central base portion 36, a sidewall 38 connected at or near the perimeter of the central base portion 36, and a perimeter lip 40 connected to the sidewall 38 opposite the central base portion 36. A pair of opposed cutouts 72 are provided in the perimeter lip 40. The cutouts 72 in the perimeter lip 40 make the container 24 smaller than a width or diameter of the patch 22 in particular regions, and expose portions of the adhesive 34 on the bottom face 32 of the web of material 26.

A pair of stiffeners 74 are provided on an upper face 30 of the web of material 26. The stiffeners 74 provide additional rigidity to the patch 22 in order to reduce flexing, bending and other undesired deformation of the microneedle array 28 prior to and during handling and deployment. In particular, the stiffeners 74 will reduce flexing in the area of the patch 22 that is suspended above the central base portion 36. As shown in FIGS. 6-8, the stiffeners 74 are parallel to each other and generally aligned relative to the sidewall 38 of the container 24. In further embodiments, more or fewer stiffeners 74 can be provided. Furthermore, the stiffeners 74 can be provided at different locations on the patch 22 than those shown in FIGS. 6-8. It should be understood that the stiffeners 74 are optional and that in certain embodiments the patch 22 may have sufficient resistance to bending or flexing without the need for additional stiffeners 74. For example, the microneedle array 28 may extend near or up to the inner surface of the sidewalls 38 and thereby provide sufficient rigidity in the suspended portion of the patch 22.

Figure 9:
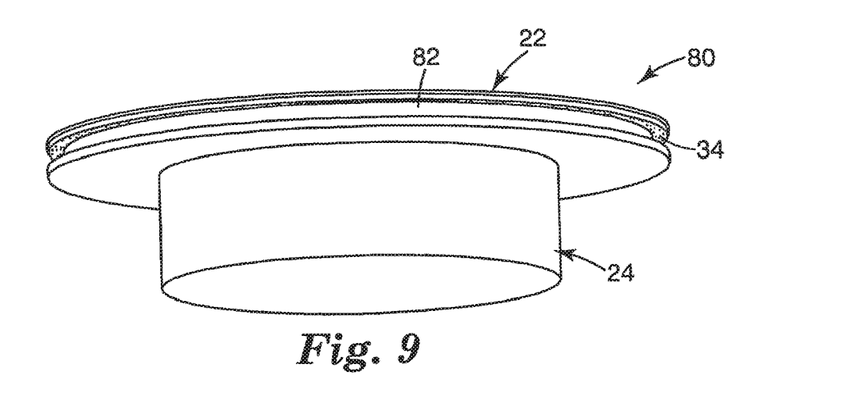
FIG. 9 is a perspective view of a third embodiment of a microneedle cartridge.
Figure 10:
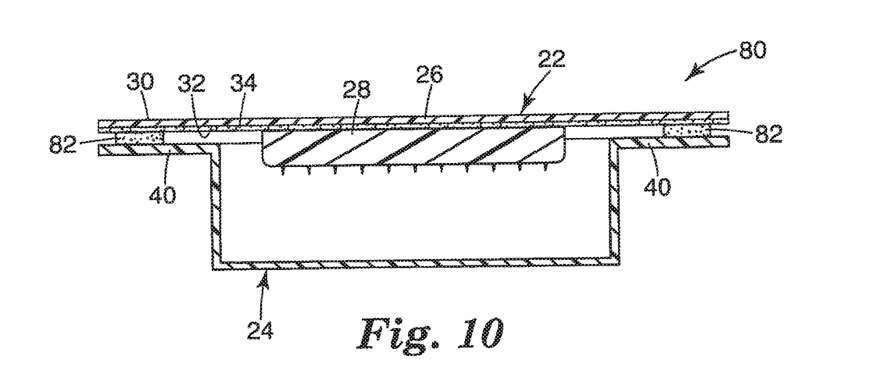
FIG. 10 is a cross-sectional view of the microneedle cartridge of FIG. 9.

FIG. 9 is a perspective view of a third embodiment of a microneedle cartridge 80. FIG. 10 is a cross-sectional view of the microneedle cartridge 80. As shown in FIGS. 9 and 10, the microneedle cartridge 80 includes a patch 22 and a container 24. The patch 22 includes a web of material 26, a microneedle array 28 and an adhesive 34 on a bottom face 32 of the web of material 26, and is generally similar to those shown and described with respect to FIGS. 1-8 above. The container is removably attached to the patch 22 to cover the microneedle array 28. The container 24 includes a circular central base portion 36, a sidewall 38 connected at or near the perimeter of the central base portion 36, and a perimeter lip 40 connected to the sidewall 38 opposite the central base portion 36. A gasket 82 is disposed to adhere to the lip 40 of the container 24 and patch (i.e., to the web of material 26 or the adhesive 34). The gasket 82 is disposed in a substantially continuous band around the microneedle array 28 in order to form a seal between the patch 22 and the container 24. In one embodiment, the gasket 82 is an adhesive. In one embodiment a different adhesive may be used for the gasket than that used for the adhesive 34 adhered to the bottom face 32 of the web of material 26.

Inserting the cartridge 80 into an applicator device can be generally similar to that described above with respect to FIGS. 1-8. Additionally, the seal formed by the gasket 82 can be broken during an inserting procedure. For example, an operator can rotate the cartridge 80 relative to an applicator device to slice or otherwise break the seal using a blade or other means disposed on the applicator device.

Figure 11:
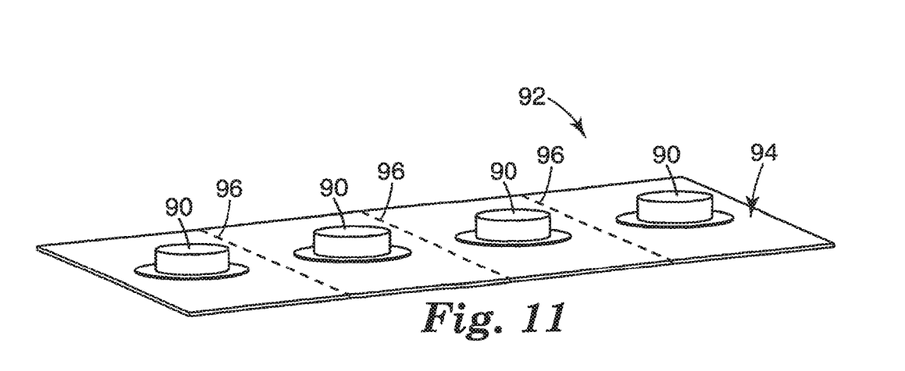
FIG. 11 is a perspective view of a number of microneedle cartridges arranged as a sheet.

A plurality of individual microneedle cartridges can be arranged as a package for providing advantages in storage, transportation and dispensing them. FIG. 11 is a perspective view of a number of microneedle cartridges 90 arranged as a sheet 92. The sheet 92 includes a liner 94 on which the cartridges 90 are carried. The individual cartridges 90 can be removably adhered to the liner 94, or secured together by other methods. In some embodiments, perforations 96 can be provided in the liner 94 for separating individual cartridges 90.

Figure 12:
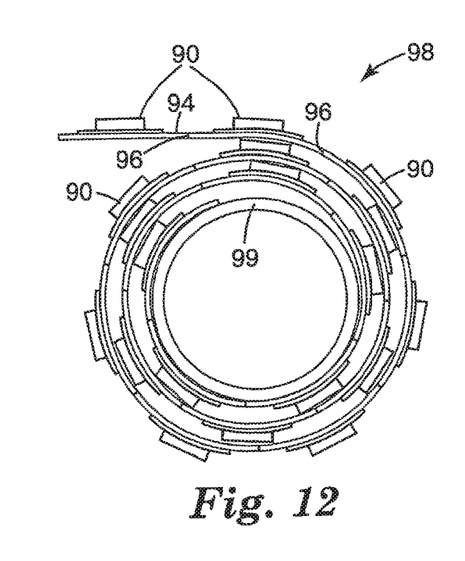
FIG. 12 is a side view of a number of microneedle cartridges arranged as a roll.

FIG. 12 is a side view of a number of microneedle cartridges 90 arranged as a roll 98. The roll 98 includes a liner 94 on which the cartridges 90 are carried and a core 99 around which the liner 94 is wound. The individual cartridges 90 can be removably adhered to the liner 94, or secured together by other methods. In some embodiments, perforations 96 can be provided in the liner 94 for separating individual cartridges 90.

The packages shown and described with respect to FIGS. 11 and 12 permit storage of a plurality of cartridges in close proximity to each other. Individual cartridges can be separated from the others as desired for use. Those packages can also help reduce time between microneedle array deployments, by facilitating "reloading" of applicator devices between array deployments.

Applicators used to apply a microneedle array or patch will typically accelerate the microneedle device to reach a desired velocity that is effective to pierce the microneedles into the skin. The desired velocity is preferably controlled to limit or prevent stimulation of the underlying nerve tissue. The maximum velocity achieved by the microneedle array upon impact with the skin is often 20 meters per second (m/s) or less, potentially 15 m/s or less, and possibly 10 m/s or less. In some instances, the maximum velocity be 8 m/s or less. In other instances, the minimum velocity achieved by the microneedle array upon impact with the skin is often 2 m/s or more, potentially 4 m/s or more, and possibly 6 m/s or more.

The microneedle arrays useful in the various embodiments of the invention may comprise any of a variety of configurations, such as those described in the following patents and patent applications, the disclosures of which are herein incorporated by reference. One embodiment for the microneedle arrays comprises the structures disclosed in United States Patent Application Publication No. 2003/0045837. The disclosed microstructures in the aforementioned patent application are in the form of microneedles having tapered structures that include at least one channel formed in the outside surface of each microneedle. The microneedles may have bases that are elongated in one direction. The channels in microneedles with elongated bases may extend from one of the ends of the elongated bases towards the tips of the microneedles. The charnels formed along the sides of the microneedles may optionally be terminated short of the tips of the microneedles. The microneedle arrays may also include conduit structures formed on the surface of the substrate on which the microneedle array is located. The channels in the microneedles may be in fluid communication with the conduit structures. Another embodiment for the microneedle arrays comprises the structures disclosed in U.S. Patent Application Publication No. 2005/0261631, which describes microneedles having a truncated tapered shape and a controlled aspect ratio. Still another embodiment for the microneedle arrays comprises the structures disclosed in U.S. Pat. No. 6,091,975 (Daddona, et al.) which describes blade-like microprotrusions for piercing the skin. Still another embodiment for the microneedle devices comprises the structures disclosed in U.S. Pat. No. 6,313,612 (Sherman, et al.) which describes tapered structures having a hollow central channel. Still another embodiment for the micro arrays comprises the structures disclosed in U.S. Pat. No. 6,379,324 (Gartstein, et al.) which describes hollow microneedles having at least one longitudinal blade at the top surface of tip of the microneedle.

Microneedle patches of the present invention may be used to deliver drugs (including any pharmacological agent or agents) through the skin in a variation on transdermal delivery, or to the skin for intradermal or topical treatment, such as vaccination.

In one aspect, drugs that are of a large molecular weight may be delivered transdermally. Increasing molecular weight of a drug typically causes a decrease in unassisted transdermal delivery. Microneedle arrays of the present invention have utility for the delivery of large molecules that are ordinarily difficult to deliver by passive transdermal delivery. Examples of such large molecules include proteins, peptides, nucleotide sequences, monoclonal antibodies, DNA vaccines, polysaccharides, such as heparin, and antibiotics, such as ceftriaxone.

In another aspect, microneedle patches of the present invention may have utility for enhancing or allowing transdermal delivery of small molecules that are otherwise difficult or impossible to deliver by passive transdermal delivery. Examples of such molecules include salt forms; ionic molecules, such as bisphosphonates, preferably sodium alendronate or pamedronate; and molecules with physicochemical properties that are not conducive to passive transdermal delivery.

In another aspect, microneedle patches of the present invention may have utility for enhancing delivery of molecules to the skin, such as in dermatological treatments, vaccine delivery, or in enhancing immune response of vaccine adjuvants.

Microneedle patches may be used for immediate delivery, that is where they are applied and immediately removed from the application site, or they may be left in place for an extended time, which may range from a few minutes to as long as 1 week. In one aspect, an extended time of delivery may be from 1 to 30 minutes to allow for more complete delivery of a drug than can be obtained upon application and immediate removal. In another aspect, an extended time of delivery may be from 4 hours to 1 week to provide for a sustained release of drug.

Although the present invention has been described with reference to several alternative embodiments, workers skilled in the art will recognize that changes may be made in form and detail without departing from the spirit and scope of the invention. For instance, various types of microneedle arrays can be utilized according to the present invention, as well as various types of microneedle applicator devices.

The invention claimed is:

1. A microneedle array cartridge comprising:
a web of material having a top face and an opposite bottom face;
an adhesive disposed on the bottom face of the web of material;
a microneedle array disposed relative to the bottom face of the web of material, the microneedle array comprising microneedles; and
a container disposed relative to the bottom face of the web of material having a perimeter lip portion, a sidewall, and a central portion for covering the microneedles of the microneedle array, wherein the sidewall is connected to the central portion and the perimeter lip portion is connected to the sidewall distal to the sidewall, wherein at least part of the perimeter lip portion contacts the adhesive and the central portion does not contact the adhesive, wherein the perimeter lip portion and the central portion are integrally formed, and wherein the perimeter lip portion of the container defines a pair of cutout regions where the perimeter lip portion does not extend as far as the web perimeter, and further comprising a pair of stiffeners disposed along the web of material.

2. The microneedle array cartridge of claim 1, wherein the at least one stiffener has an elongate shape.

3. The microneedle array cartridge of claim 1, wherein the at least one stiffener of the pair of stiffeners has a length at least as long as a width or diameter of the central portion of the container.

4. The microneedle array cartridge of claim 1, wherein the web of material defines a web perimeter, and wherein at least a portion of the perimeter lip portion of the container generally extends at least to the web perimeter.

5. The microneedle array cartridge of claim 1, and further comprising a gasket disposed between the web of material and the perimeter lip portion of the container for forming a seal.

6. The microneedle array cartridge of claim 1, wherein the array and web of material are integrally formed.

7. A microneedle array cartridge comprising:
a web of material having a top face and an opposite bottom face;
an adhesive disposed on the bottom face of the web of material;
a microneedle array disposed relative to the bottom face of the web of material, the microneedle array comprising microneedles; and
a container disposed relative to the bottom face of the web of material having a perimeter lip portion, a sidewall, and a central portion for covering the microneedles of the microneedle array, wherein the sidewall is connected to the central portion and the perimeter lip portion is connected to the sidewall distal to the sidewall, wherein at least part of the perimeter lip portion contacts the adhesive and the central portion does not contact the adhesive, wherein the perimeter lip portion and the central portion are integrally formed, and wherein the perimeter lip portion of the container defines a pair of cutout regions where the perimeter lip portion does not extend as far as the web perimeter, and further comprising at least one stiffener disposed along the web of material, wherein the at least one stiffener has a length at least as long as a width or diameter of the central portion of the container.

8. The microneedle array cartridge of claim 7, wherein the at least one stiffener has an elongate shape.

9. The microneedle array cartridge of claim 7, wherein the at least one stiffener has a length at least as long as a width or diameter of the central portion of the container.

10. The microneedle array cartridge of claim 7, wherein the web of material defines a web perimeter, and wherein at least a portion of the perimeter lip portion of the container generally extends at least to the web perimeter.

11. The microneedle array cartridge of claim 7, and further comprising a gasket disposed between the web of material and the perimeter lip portion of the container for forming a seal.

12. The microneedle array cartridge of claim 7, wherein the array and web of material are integrally formed.

* * * * *

UNITED STATES PATENT AND TRADEMARK OFFICE
CERTIFICATE OF CORRECTION

PATENT NO. : 10,307,578 B2
APPLICATION NO. : 15/606753
DATED : June 4, 2019
INVENTOR(S) : Frank Frederickson et al.

Page 1 of 1

It is certified that error appears in the above-identified patent and that said Letters Patent is hereby corrected as shown below:

In the Specification

Column 1
Line 8 (approx.), delete "11/917,412," and insert -- 11/917,442, --, therefor.

Column 7
Line 19, delete "60/694,447" and insert -- 60/694,447 (Attorney Docket No. 60874US002) --, therefor.

Column 10
Line 33 (approx.), delete "charnels" and insert -- channels --, therefor.

Column 11
Line 10, delete "pamedronate;" and insert -- pamidronate; --, therefor.

In the Claims

Column 12
Line 3, in Claim 3, after "wherein" delete "the".

Signed and Sealed this
Twenty-fifth Day of February, 2020

Andrei Iancu
*Director of the United States Patent and Trademark Office*